United States Patent
Bock-Krausen et al.

(10) Patent No.: US 9,582,079 B2
(45) Date of Patent: Feb. 28, 2017

(54) MANUALLY OPERATED ROBOT CONTROL SYSTEM AND METHOD FOR CONTROLLING A ROBOT SYSTEM

(71) Applicant: ABB gomtec GmbH, Seefeld (DE)

(72) Inventors: Leopold Bock-Krausen, München (DE); Bernd Gombert, Wörthsee (DE)

(73) Assignee: ABB GOMTEC GMBH, Seefeld (DE)

( * ) Notice: Subject to any disclaimer, the term of this patent is extended or adjusted under 35 U.S.C. 154(b) by 28 days.

(21) Appl. No.: 14/438,692

(22) PCT Filed: Oct. 21, 2013

(86) PCT No.: PCT/EP2013/071916
§ 371 (c)(1),
(2) Date: Apr. 27, 2015

(87) PCT Pub. No.: WO2014/064025
PCT Pub. Date: May 1, 2014

(65) Prior Publication Data
US 2015/0293596 A1 Oct. 15, 2015

(30) Foreign Application Priority Data
Oct. 25, 2012 (DE) .................. 10 2012 110 190

(51) Int. Cl.
*G06F 3/01* (2006.01)
*G05B 19/427* (2006.01)
(Continued)

(52) U.S. Cl.
CPC .............. *G06F 3/017* (2013.01); *A61B 34/30* (2016.02); *A61B 34/37* (2016.02); *B25J 9/1697* (2013.01);
(Continued)

(58) Field of Classification Search
CPC ....... G05B 19/427; G06F 3/017; A61B 34/30; A61B 34/37; A61B 34/35; A61B 34/70;
(Continued)

(56) References Cited

U.S. PATENT DOCUMENTS 6,026,720 A * 2/2000 Swank .................. B23B 31/202
82/128
8,330,639 B2 * 12/2012 Wong .................. G06F 3/03547
341/173

(Continued)

FOREIGN PATENT DOCUMENTS

DE 198 09 382 A1 10/1998
KR 10-2011-0003146 A 1/2011
(Continued)

OTHER PUBLICATIONS

German Office Action dated Jul. 3, 2013 in corresponding German Application No. DE 102012110190.6.
(Continued)

*Primary Examiner* — Abby Lin
(74) *Attorney, Agent, or Firm* — Carter, DeLuca, Farrell & Schmidt, LLP

(57) ABSTRACT

The invention relates to a device (2, 6) for manually controlling a robot system, comprising an input device (2), which can be operated by means of at least two hands and has a sensor system (7, 10) for detecting control specifications of a first hand (12) and control specifications of a second hand (13). According to the invention, the control device (2, 6) comprises a first control unit (19), which performs a position control function in dependence on the control specifications of the first hand (12), and a second control unit (20), which performs a velocity control function or a position control function in dependence on the control specifications of the second hand (13).

9 Claims, 6 Drawing Sheets

(51) Int. Cl.
   *A61B 34/30*    (2016.01)
   *B25J 13/02*    (2006.01)
   *B25J 9/16*     (2006.01)

(52) U.S. Cl.
   CPC ............ *B25J 13/02* (2013.01); *G05B 19/427* (2013.01); *A61B 2034/301* (2016.02); *A61B 2034/302* (2016.02)

(58) Field of Classification Search
   CPC .............. A61B 34/74; A61B 2034/401; A61B 2034/402; A61B 2017/00207; A61B 2017/00212; B25J 9/1697; B25J 9/1689; B25J 13/02; B25J 13/065; B25J 13/04; B25J 19/06
   See application file for complete search history.

(56) References Cited

U.S. PATENT DOCUMENTS

| | | | | |
|---|---|---|---|---|
| 8,464,160 | B2* | 6/2013 | Sakata | G06F 1/1601 345/158 |
| 8,760,426 | B1* | 6/2014 | Strand | G09G 5/00 345/169 |
| 2005/0045409 | A1* | 3/2005 | Fenelli | B62D 51/04 180/326 |
| 2006/0229034 | A1* | 10/2006 | Gizis | A63H 30/04 455/95 |
| 2007/0236460 | A1 | 10/2007 | Young et al. | |
| 2008/0150468 | A1* | 6/2008 | Kalender | G05B 19/416 318/650 |
| 2008/0255704 | A1* | 10/2008 | Braut | B25J 13/02 700/264 |
| 2009/0158190 | A1* | 6/2009 | Higginson | G06F 3/0481 715/773 |
| 2010/0332087 | A1* | 12/2010 | Claffee | B25J 3/04 701/49 |
| 2011/0118752 | A1 | 5/2011 | Itkowitz et al. | |
| 2011/0128363 | A1* | 6/2011 | Mizutani | G06F 3/017 348/77 |
| 2011/0296353 | A1 | 12/2011 | Ahmed | |
| 2012/0157198 | A1* | 6/2012 | Latta | A63F 13/803 463/31 |
| 2013/0290911 | A1* | 10/2013 | Praphul | G06F 3/017 715/863 |

FOREIGN PATENT DOCUMENTS

| | | |
|---|---|---|
| WO | 2008/064380 A1 | 6/2008 |
| WO | 2012/024022 A2 | 2/2012 |
| WO | 2012/099584 A1 | 7/2012 |

OTHER PUBLICATIONS

International Search Report issued in corresponding application No. PCT/EP2013/071916 on Feb. 18, 2014.

* cited by examiner

MANUALLY OPERATED ROBOT CONTROL SYSTEM AND METHOD FOR CONTROLLING A ROBOT SYSTEM

CROSS-REFERENCE TO RELATED APPLICATIONS

This application is a U.S. National Stage Application filed under 35 U.S.C. §371(a) of International Application No. PCT/EP2013/071916 filed Oct. 21, 2013, which claims the benefit of and priority to German Patent Application No. 10 2012 110 190.6 filed Oct. 25, 2012, the entire contents of which are incorporated by reference herein.

The invention relates to a device for controlling a robot system according to the preamble of claim 1, to a use of such a device according to the preamble of claim 7 and also to a method for controlling a robot system according to the preamble of claim 9.

Known robot systems, to which reference shall be made in the following, comprise an input device, such as a joystick or an imaging system, which is manually operated by a user. The control instructions input by the user are converted by the input device into corresponding control commands, which are carried out by one or more robots. Depending upon the design, the known input devices are equipped with various sensors, which detect the control instructions of the user and convert them into corresponding control signals. The control signals are then further processed in control circuits or regulatory loops, which subsequently generate drive signals with which the actuators of a robot or of a tool mounted on the robot are controlled, such that the robot or the tool carries out the task desired by the user.

Owing to the complexity of many robot systems, the robots are often operated by both hands simultaneously. In doing so the user must carry out a first control function, e.g., a movement of the robot head in a first plane, with one hand and a second control function, e.g., a movement of the robot head in a second plane or an actuation of a tool attached to the robot, with the other hand.

Known to the prior art, for example, are robot systems that have an input device with two joysticks, which the user can operate with his left or right hand. The displacement of the joysticks is recorded by a sensor system, typically by potentiometers, and the robots are controlled accordingly. The robot is thus velocity-controlled or regulated. In other words, a specific displacement of the joystick is converted into a specific velocity with which the robot is driven in the respective spatial coordinate. In a given joystick position, the robot thus moves at a certain speed. If the user wishes to stop the robot, then he must take back the displacement of the joystick and shift the joystick into the zero position. With such a system, however, only a general or "rough" maneuvering of the robot into a particular position is possible. For the precise control of a robot, which is in particular necessary for high-precision applications (e.g., in the field of robot-supported surgery), the velocity control method takes a great deal of getting used to and requires extensive practice. One of the key reason for this lies in that the robot will continue to move as the user is returning the joystick to the zero position, until the zero position is actually reached. The user would therefore have to learn how the robot performs in all operating states and make manual adjustments. The level of control achievable by humans, however, is considerably less than that of machines.

US 2010/0332087 A1 discloses a device for controlling a robot system with a manually operable input device, which has a sensor system for recording control instructions of a first hand and of a second hand. The device furthermore has a first control unit (MASTER ARM), which performs a position control function in dependence on the control instructions of a first hand, and a second control unit (DRIVE CONTROLLER), which performs a velocity control function in dependence on the control instructions of a second hand. However, the known device fails to take the handedness of a user into account.

US 2008/0255704 A1 discloses a device for controlling a robot system with a manually operable input device, which has a sensor system (joysticks) for recording control instructions of a first hand and a second hand. The joysticks can be configured differently for left- or right-handed users. For example, the movement axes of the joysticks can be adjusted to suit the preference of the user.

Other control devices for robots are disclosed in DE 198 09 382 A1, US 2011/0296353 A1 and US 2011/0118752 A1.

Hence the object of the present invention is to create a device for controlling a robot system that is operable by left-handed as well as right-handed users and which enables a considerably more precise control of the robot system or of a component of the robot system.

According to the invention, this object is achieved by the features listed in claims 1, 7 and 9. Other embodiments of the invention arise from the subordinate claims.

According to the invention, a device for controlling a robot system is proposed, which has a manually operable input device that has a sensor system for recording control instructions of at least a first hand and a second hand. The device of the invention further comprises a control that converts the control instructions into corresponding drive signals with which one or more actuators of the robot system are controlled. According to the invention, the control comprises at least two control units, wherein a first control unit performs a position control function in dependence on the control instructions of the first hand and a second control unit performs a velocity control function in dependence on the control instructions of the second hand. Moreover, an appliance is provided for recognizing a dominant hand and a non-dominant hand of a user, wherein the control takes information on the handedness of the user generated by the appliance into account and automatically performs a position control function in response to control instructions of the dominant hand and automatically performs a velocity control function in response to control instructions of the non-dominant hand. As described above, robots that are controlled purely by a velocity control function are relatively hard to manipulate. Only very experienced and skilled users are capable of operating such robots by, for example, first maneuvering the robot into the general target position and then carefully zeroing in on the desired target position with repeated brief movements of a joystick. In contrast, position controls are considerably easier and more intuitive to operate. With the help of the position control function, as a rule the user can navigate to a desired target point considerably faster and more accurately, and without lengthy practice beforehand. The manipulation of a robot system with at least one position control function is thus considerably easier and more precise.

In the context of this document, "robot system" means in particular a technology system with one or more robots, which can further comprise one or more robot-actuated tools and/or one or more other machines. For instance, a robot system equipped for use in minimally invasive surgery can comprise one or more robots, which are each fitted with a surgical instrument or with another tool, as well as an electrically adjustable operating table.

In the context of this document, "robot" means any machine with one or more articulated arms or other movable elements that can be moved by one or more actuators such as electric motors.

Examples of suitable input devices for controlling a robot system can include: joysticks, mouse devices, keyboards, control panels, touch panels, touch screens, and/or camera-supported image processing systems, as well as all other known input devices that can record control instructions of a user and generate corresponding control signals.

In the context of this document, "velocity control function" means a control or regulator function that converts a control instruction (e.g., a hand motion or a displacement of a joystick) performed by a user into a movement of the controlled object at a corresponding velocity. In contrast, "position control function" means a control or regulator function that converts a control instruction performed by a user into a corresponding change in the position of the controlled object. The position of the hand or of the manually operated input device thus determines the position of the controlled object. The control instruction of the user is converted with a pre-specified scaling factor into a corresponding movement of the controlled object.

According to the invention, the input device can have the same or different input means for the first and second hands of the user. For example, the user is thus able to operate a joystick or an imaging system with each hand, or operate a joystick with one hand and an imaging system with the other hand. In another example, the user could operate an imaging system with one hand and a mouse or other input means with the other hand. The number of degrees of freedom of the input means operated by the user can be the same or different. Preference is given to the input device of the invention also being able to process control instructions from more than two hands.

According to a preferred embodiment of the invention, the input device comprises at least one imaging system, which converts the hand motions of a user and/or manual gestures and/or movements of other body parts, e.g., the arms or feet, into corresponding control signals. Such a system is described in, for example, US 2011/296353 A1 and can be used according to the invention. This system has a camera, which can record various gestures of a user within an imaging zone. The recorded gestures can be compared with a database, for example, in which various known gestures are stored. If the recorded gesture matches the known gesture, a control command allocated to the known gesture will be triggered. The use of such a system for controlling a robot is disclosed in KR 10-2011-0003146, for example.

In principle, any of the components of a robot system (henceforth "objects") can be controlled by the device of the invention. Examples of such components not only include robots of any design and robot-actuated tools, but also any other machines or individual parts of an object. For example, the first and second control units can be provided for controlling the same actuator or actuators of one or more robots and/or of one or more tools and/or of one or more machines. As an alternative, the first and second control units can be designed for controlling one or more actuators of one or more objects. For example, the first control unit can be designed for positioning a robot head or a tool held by the robot, and the other control unit can be designed for operating the tool.

The allocation of a control instruction executed by the user to the controlled object and/or actuator can preferably be adjusted. For example, the control instructions of one hand can thus be converted into a specific movement of the robot head, and the control instructions of the other hand can be converted into a movement of a tool. In another example, the movements of both hands can be converted into corresponding coarse or fine movements of a robot head or of the same component. Furthermore, provision can be made such that different control instructions of the same hand or of the same body part (e.g., up/down and left/right motions) control different components. The respective allocation of a control instruction to the action executed by the system can preferably be set by the user, for example by inputting data in an input mask of a control software, by making the appropriate selection on a control panel, or by performing special gestures that will be recognized by an imaging system and interpreted as corresponding commands, in addition to many other possibilities.

As mentioned previously, one of the control units can perform a position control function and the other control unit can perform a velocity control or position control function. When both control units perform a position control function, the scaling factor with which a manually executed control instruction is converted into a corresponding movement of the controlled object will preferably be different for each control unit. The user can thus perform a coarse control function with one hand and a fine control function with the other hand. The scaling factor of the individual control units is preferably adjustable.

If both control units are intended to control the same actuator or actuators, the first and second control signals generated by the input device, or signals generated from those signals, will preferably be superimposed to form an output or drive signal, by means of which the desired actuator or actuators will be controlled.

According to an embodiment of the invention, the control device comprises an appliance for recognizing a dominant hand and/or a non-dominant hand. If for example the user is right-handed, the control device of the invention would recognize the right hand as the dominant hand and the left hand as the non-dominant hand. For example, the appliance for recognizing the dominant or non-dominant hand, respectively, can comprise a facial recognition device that compares a user photographed by the camera with stored data and is thus able to identify him/her. If the stored data also contains information on handedness (left handedness, right handedness, ambidextrousness), the handedness of the user can be recognized automatically. As an alternative, the imaging system could recognize certain gestures that the user must perform in order to indicate the dominant or non-dominant hand, respectively, to the system. The dominant or non-dominant hand of the user could also be tagged with a ring or a colored marker, for example, in order to indicate the dominant or non-dominant hand, respectively, to the system. Another possibility for recognizing the dominant or non-dominant hand comprises an input device (e.g., an input panel or software input mask) on which the user can input his dominant or non-dominant hand. The control instructions executed by the dominant hand and the non-dominant hand will then converted by the input device into corresponding signals and transmitted by signal processing means to the first and second control units, respectively.

According to a preferred embodiment of the invention, the control signals representing the control instructions of the dominant hand are fed to and processed by a first control unit. The control signals representing the control instructions of the non-dominant hand are preferably fed to and processed by a second control unit. The aforementioned allocation will preferably be maintained, even when different users with different handedness use the robot system. Hence the first control unit always processes the control instructions of the dominant hand and the second control unit always processes the control instructions of the non-dominant hand. The first control unit preferably executes a position control function; the second control unit a velocity or position control function.

In order to ensure that the dominant/non-dominant hand is always allocated to a specific control unit, provision is made of suitable means (e.g., a switch mechanism) that will automatically switch the output signals of the input device or the input signals of the control units if the handedness of the user changes. The control signal representing the control instructions of the dominant hand thus always reaches the input of the same control unit (the first control unit, for example) and the control signal representing the control instructions of the non-dominant hand always reaches the input of the other control unit (the second control unit, for example). For example, the user will therefore always perform a fine control (by means of a position control function) with his dominant hand and a coarse control (by a velocity or position control function) with his non-dominant hand, regardless of whether he is right-handed or left-handed.

A tool controllable by the control device of the invention preferably comprises at least one articulation. The tool can be, for example, a gripping, retaining, cutting, sawing, grinding, connecting, joining, or other tool, in particular one from the group comprising surgical instruments.

According to a preferred embodiment of the invention, the control device is configured such that a tool is actuated (i.e., positioned and possibly operated as well) by the user's dominant hand, and another object of the robot system is controlled by the user's non-dominant hand, applying a velocity control function to assist with the work process performed with the tool. For example, a doctor can thus operate a surgical instrument with his dominant hand and the robot arm to which the instrument is attached with his non-dominant hand, or he can control a second robot arm, an operating table, or another device for adjusting the position of the patient's body or body part such as a knee. With the combination of position control and velocity control functions it is possible to perform a surgical intervention in a particularly precise and intuitive manner.

The input device of the invention is preferably configured in such a way that, in addition to hand motions or manual gestures, movements of other body parts (e.g., of the arms, legs, head, eyes, and/or mouth) can also be recognized. In this case the control device is configured such that the movements of the other body part or parts will be converted into corresponding actions of the robot system. In principle, any control instructions from any of the user's body parts can be allocated to individual objects or actuators of the robot system.

In control technology, a distinction is typically made between open-loop control and closed-loop control. In this document, however, the term control and its various grammatical forms shall be used for both terms and their various grammatical forms, unless expressly stated otherwise. In other words, no explicit distinction will be made between open-loop and closed-loop control. It is obvious to persons skilled in the art that they can design the respective control devices as either open-loop or closed-loop devices.

BRIEF DESCRIPTION OF THE DRAWINGS

In the following, the invention will be explained in more detail, with reference to the appended drawings as examples. Shown are.

EMBODIMENTS OF THE INVENTION

Figure 1:
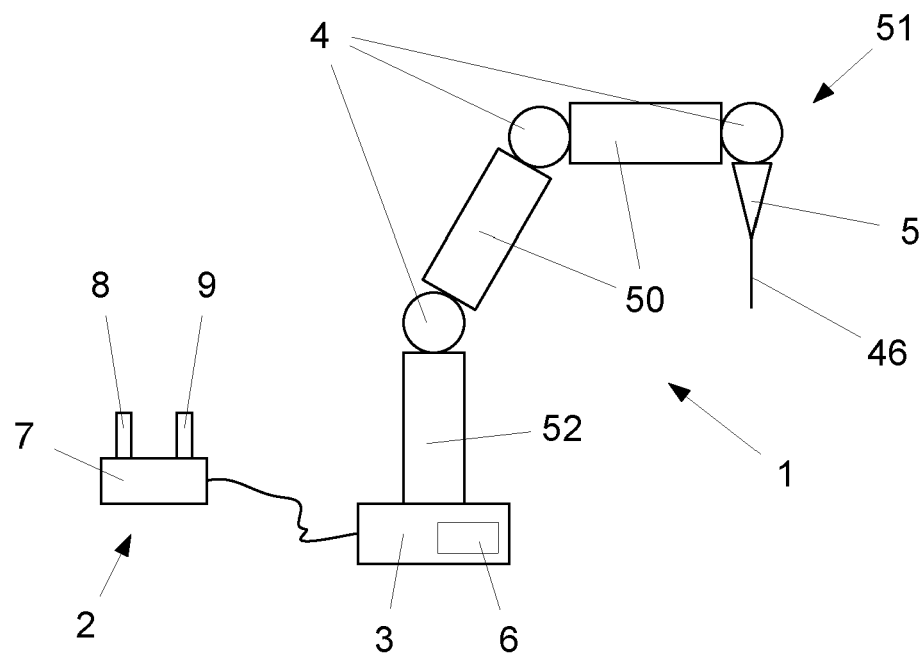
FIG. 1 a robot system according to a first embodiment of the invention.

FIG. 1 shows a robot system that can be used for industrial purposes as well as in the medical field, for example as a surgical robot, in particular for minimally invasive surgery. The robot system comprises a robot 1 with, e.g., two articulated arms 50, which are each connected together via one or several joints 4. The individual joints are each operated by a motor, in this case an electric motor (not shown) and depending on the design, can effect a pivoting and/or rolling motion of the arms 50. The number of joints 4 thus determines the number of degrees of freedom of the robot arm.

The robot arm has a fixed end 52, which is fastened onto a base 3, and a freely movable end, which can also be designated as the robot head 51. On the robot head 51 is fastened a tool 5, which is matched to the intended use of the robot 1. For industrial applications, for example, provision can be made of a grinding, boring, screwing, milling, clamping, or welding tool, as well as many other possibilities. For the surgical use of the robot, the robot head 51 can be equipped with, for example, an endoscope, a laparoscopic instrument, a cutting, gripping, holding, connecting, suturing, or other surgical tool or instrument, in particular for minimally invasive surgery. The actual end effector of the tool 5, e.g., a scalpel, scissors, needle, scraper, file, gripper, etc., is designated with the reference 46.

The robot system illustrated in FIG. 1 is controlled by an input device 2, which in this case comprises a control console 7 with two joysticks 8, 9. The two joysticks 8, 9 can be manually operated by a user with both hands. The displacement of each of the joysticks 8, 9 is recorded by sensors and converted into corresponding electric signals. The output signals of the control console 7 are transmitted to an electronics assembly with a robot control 6 integrated in the base 3, which converts the control signals received from the control console 7 into corresponding drive signals for the individual actuators of the robot 1 so that the robot arm moves in the manner specified by the user. The tool 5 fastened to the robot head 51 can thus be maneuvered to any given point within the reach of the robot arm.

Furthermore, the tool 5 itself can also be operated by the control console 7. If the tool 5 has one or more articulations, the user can execute, for example, a tilting, pivoting, or turning movement for bringing the end effector 46 into a desired position, or for performing a desired action such as incision, irradiation, gripping, suturing, etc.

Here, the control console 7 is designed for left-handed as well as right-handed users. The allocation as to which of the two joysticks 8, 9 is provided for the dominant or non-dominant hand, respectively, is preferably freely adjustable in order to enable both left-handed and right-handed users to operate the input device 2.

In dependence on this allocation, various control or regulation modes will be executed upon actuation of the joysticks 8, 9, wherein, for example, fine positioning by position control can be performed with the joystick 9 operated by the dominant hand 12 and coarse positioning by velocity control can be performed with the joystick 8 operated by the non-dominant hand 13, as will be explained in more detail further below. In this manner, for example, the robot arm 1 could be coarse-positioned with the joystick 8 operated by the non-dominant hand and the end effector 5 could be fine-positioned with the joystick 9 operated by the dominant hand.

Although the allocation of the control instructions executed by the user and the respective response of the robot system can be fixed, it is preferably freely adjustable. For example, it would be possible to set the left joystick 8 to control the robot arm and the right joystick 9 to control the end effector 46. As an alternative, both joysticks 8, 9 could control the robot arm and/or the end effector 46. For the case in which the robot arm is controlled by both joysticks, the robot arm could be coarse-positioned with, say, the left joystick 8 and fine-positioned with the right joystick 9. The reference point of the control does not necessarily have to be the robot head 51 or the end effector 46. According to a special embodiment of the invention, for example, it is also possible to control individual actuators of the robot system separately.

Figure 2:
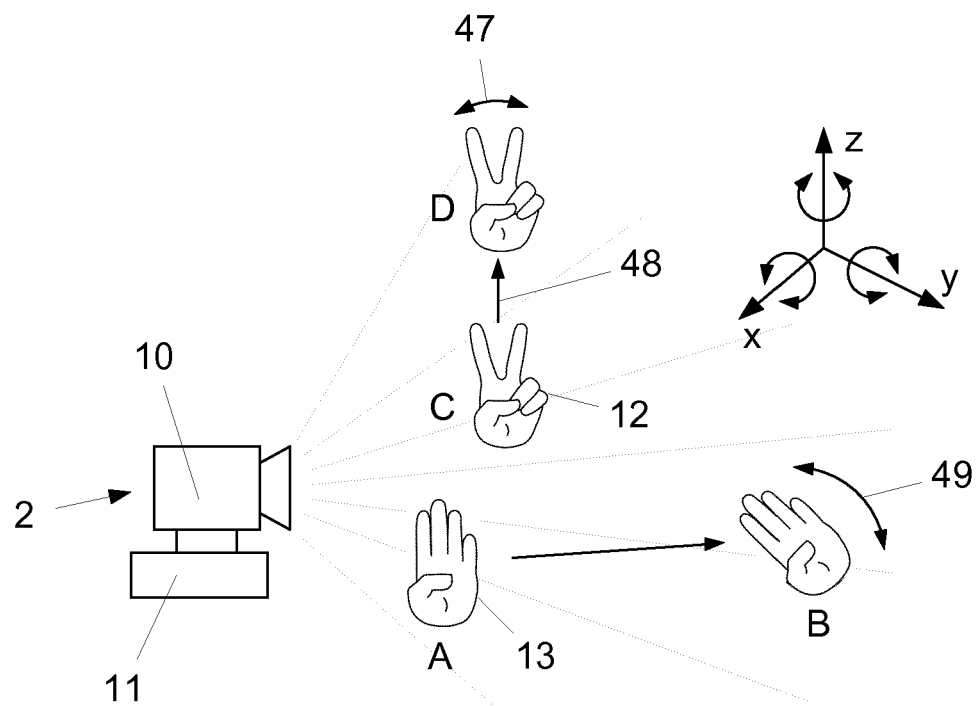
FIG. 2 an imaging system and various control instructions performed by a user.

FIG. 2 shows an alternative input device 2 for a robot system. In this case, the input device 2 comprises an imaging system with a camera, in particular a 3D camera 10, and an electronic assembly 11 with image processing software. During operation the camera 10 continuously records images, which are processed by the image processing software. The image processing software has the capacity to recognize the hands 12, 13, the face, or body parts of the user, or manually operated objects or devices such as a pointer, a scissors, a knife, etc., and to generate corresponding control signals in response to control instructions executed by the user.

Shown schematically in FIG. 2 are the left and right hands 13 and 12, respectively, of a user, which are recorded by the camera 10. For controlling the robot system, the user can in principle perform movements in all three Cartesian spatial coordinates (x, y, z) as well as rotational movements about any spatial axis. Furthermore, the user can also perform certain gestures for controlling or configuring the robot system. Static gestures (e.g., hand signals) as well as dynamic gestures (e.g., hand wave) can be recorded and interpreted as such by the input device 2.

In the example illustrated, the user moves his left hand 13 from point A to point B while simultaneously tilting back his hand 13, as indicated by an arrow 49. This movement is recognized and converted into corresponding control signals by the image processing software. Depending upon the configuration of the robot system, the position and/or location of the end effector 46, for example, can be influenced in a manner corresponding with such a movement. However, individual actuators of the robot arm 1 or of the tool 5 could also be controlled separately. For instance, by moving the hand 13 in a linear direction from point A to point B, a first articulation 4 of the robot arm or of the tool 5 could be actuated, and a second articulation 4 of the robot arm or of the tool 5 could be actuated by the tilting movement of the hand 13. As already mentioned, the resulting action of the robot system in response to a control instruction is preferably freely configurable. Preference is given to providing a suitable software program with an input mask or other input unit for this purpose.

In the example illustrated, the user's right hand 12 executes a cutting movement by moving the index finger and the middle finger of the hand 12 in a manner similar to cutting with scissors (see arrow 47). The user also moves his hand 12 forwards in the cutting direction 48 (from point C to point D), in order to make, for example, an incision during an operation. The electronics assembly 11 in turn recognizes the cutting movement 47 and the forward movement 48 and converts them into corresponding control signals, which are fed to and further processed by the robot control 6. The robot control 6 then generates one or more drive signals l1-l3 (see FIG. 6 or FIG. 8), with which certain actuators of the robot system are controlled such that the surgical instrument attached to the robot head 51 follows the control instructions of the user and makes the desired incision.

As already mentioned, the robot system could also be controlled with, for example, a manually actuated object, a user-actuated mechanism, or by other body parts such as the feet. In this case the imaging system 10, 11 would have to recognize the respective control means and convert the movement performed by the user into corresponding signals.

The imaging system 10, 11 is preferably designed not only for recognizing movements but also for recognizing gestures. This also makes it possible to control or configure the robot system by certain gestures. For recognizing a gesture, the gestures recorded by the input device 2 can be compared with, for example, the gestures stored in a database (not shown). If a recorded gesture matches a gesture stored in the database, a control command allocated to the gesture can be carried out.

The gesture database can be contained in the electronics assembly 11, for example. The electronics assembly 11 with the image recognition software can be part of the input device 2 or it can also be implemented elsewhere, for instance in a separate microcontroller, or combined in a single control unit together with the robot control 6.

Figure 3:
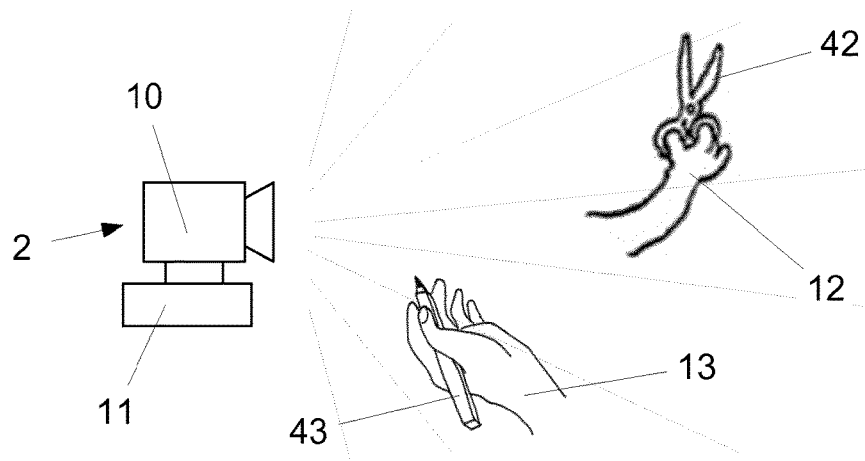
FIG. 3 an imaging system and various control instructions performed by a user.

FIG. 3 shows an imaging system 10, 11 being used as an input device 2 for controlling a robot system. In this exemplary embodiment, the robot system can be controlled by various objects that the user holds in at least one of his two hands 12, 13. In FIG. 3 the user is holding a pencil 43 with a mark, label, etc., in his non-dominant hand 13 and scissors 42 in his dominant hand 12. The mark on the pencil 43 and the scissors 42 as well can be effectively recognized and the movement thereof accordingly effectively tracked by the imaging system 10, 11. The control instructions of the user can therefore be converted into corresponding control movements in a very rapid and precise manner. For example, cutting movements performed by the user can be translated into corresponding cutting actions of a surgical instrument. It is obvious to persons skilled in the art that in lieu of a pencil 43 or scissors 42, any other objects or input devices can be guided by hand.

The robot control 6, which processes the control signals emitted by the input device, is preferably designed such that the control instructions performed by one hand (e.g., 12) will be converted by a position control function into corresponding movements of the robot system and the control instructions performed by the other hand (e.g., 13) will be converted by a velocity control function into corresponding movements of the robot system. Optionally, however, provision could also be made of a position control function for both hands. The robot control 6 will be explained further below, with reference to FIGS. 6 and 8 as examples.

Figure 4:
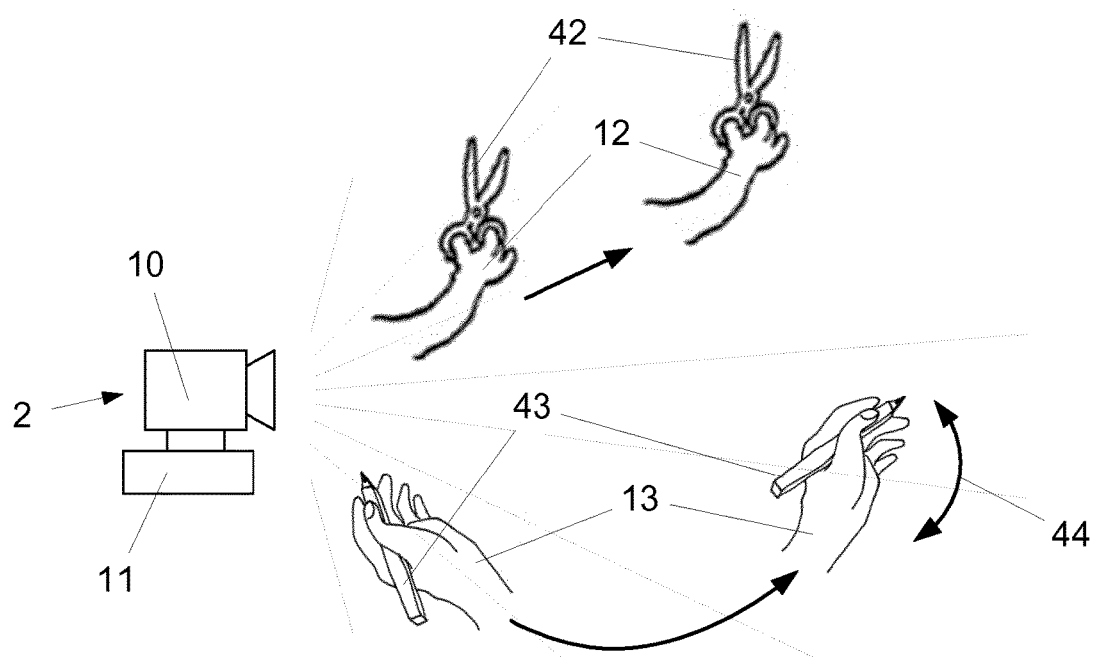
FIG. 4 an imaging system and various control instructions performed by a user.

FIG. 4 shows another manual control scenario for a robot system. In this scenario, the hand motions and/or gestures of the right and left hands 12, 13, including the input devices 42, 43, are likewise recorded by an imaging system 10, 11 and converted into corresponding control signals. The robot control 6 processes the control signals and, on the basis of the motions of the hands 12, 13 and/or of the input devices 42, 43, then generates one or more drive signals l1-l3 (see FIG. 6 or FIG. 8, for example) with which certain actuators of the robot system are operated such that the tool 5 attached to the robot head 51 follows the control instructions of the user and carries out a desired action.

In the present example, a velocity control function is performed in dependence on the control instructions of the non-dominant hand 13 and a position control function is performed in dependence on the control instructions of the dominant hand 12. A specific movement of the non-dominant hand 13 from a starting or neutral position effects a movement of the controlled object at a specific speed that depends upon the extent of the hand movement. Depending upon the configuration, the user can control the velocity of, e.g., a certain joint 4, the robot head 51, a tool 5, or another component of a robot system. In order to stop the controlled object, the hand must be moved back into the neutral position. In addition to a linear movement, a rotation of the hand 13 can likewise be converted into a corresponding velocity of the controlled object, as represented by an arrow 44.

In contrast, the control instructions of the dominant hand 12 are implemented by a position control function. In other words, a spatial movement of the dominant hand 12 is converted by the robot system into a corresponding movement of the controlled object, wherein the location of the input devices (e.g., of the hand or of a hand-actuated object) correlates with the location of the controlled object. The controlled object thus essentially follows the hand motion, or rather the control instruction. In order to stop the controlled object, the hand 12 merely has to be held stationary.

Figure 5:
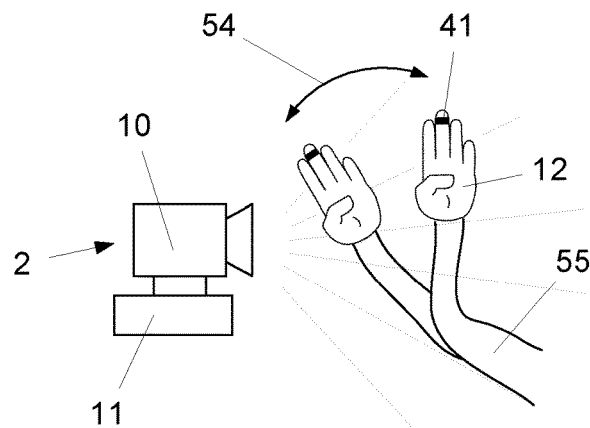
FIG. 5 an imaging system and an option for identifying a dominant or non-dominant hand.

FIG. 5 shows a special embodiment of the invention in which the input device 2 can automatically distinguish the dominant hand 12 from the non-dominant hand 13 of the user. For example, if the user is right-handed, the input device 2 would recognize the right hand 12 as the dominant hand and the left hand 13 as the non-dominant hand. For automatic recognition of handedness, the electronic analysis system 11 can comprise, for example, facial recognition software with which the user can be identified. The handedness of the identified person can then easily be determined if the handedness (right-handedness or left-handedness or ambidextrousness) of the individual users is also stored in the database.

As an alternative, the user could also be prompted to perform a certain gesture with his dominant hand 12 and/or with his non-dominant hand 13, or to hold the respective hand in the recording zone of the imaging system 10 when prompted to do so. Optionally, the user could also input data into an input mask displayed on a screen, in addition to many other possibilities.

In the present exemplary embodiment, the dominant hand 12 of the user is tagged with a marker, e.g., a ring 41. Optionally, however, provision could also be made of a color marker or any other kind of marker (e.g., a glove) recognizable by the imaging system 10, 11. If the user uses an object or other input devices 42, 43, obviously the object or the input devices 42, 43 can also be tagged.

After the recognition and allocation, respectively, of the dominant and/or non-dominant hand 12, 13 of the user, the robot system can be manually controlled. The actions executed by the hands 12, 13 are recorded by the input device 2 and the corresponding control signals S1, S2 are transmitted to a robot control 6, as illustrated in example form in FIG. 6. The robot control 6 comprises a first control unit 19, which processes the control signals S1 of the non-dominant hand (e.g., the left hand 13), and a second control unit 20, which processes the control signals S2 of the dominant hand (e.g., the right hand 12).

The control of the invention further comprises a unit 45, which always automatically applies the control signals S2 of the dominant hand 12 to the input 14 of the second control unit 20 and the control signals S1 of the non-dominant hand 13 to the input 15 of the first control unit 19. For example, if the non-dominant hand 13 generates the signal S1 and the dominant hand 12 generates the signal S2, then both signals are simply looped through on the corresponding inputs 14, 15 of the control units 19, 20. However, if the dominant hand 12 generates the signal S1 and the non-dominant hand 13 generates the signal S2 (owing to the allocation of the hands in the recording system 2, for example), then the assignment of the inputs 14, 15 of the control units 19, 20 is preferably switched automatically. For example, the switching unit 45 can have switches or it can be configured as a software program. The unit 45 can be integrated in the robot control 6, in the input device 2, or in another place such as an external computer, for example.

Figure 6:
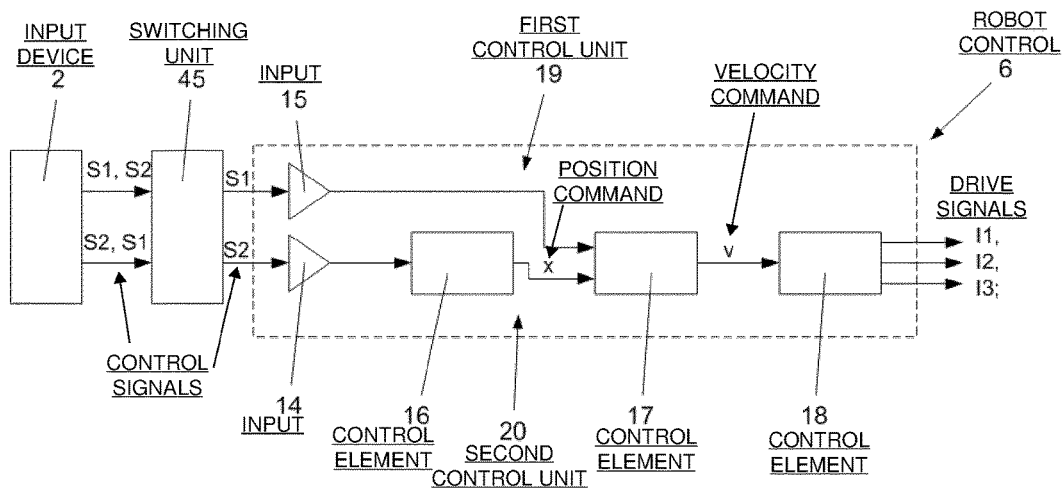
FIG. 6 a robot control for a robot according to FIG. 1.

In the exemplary embodiment illustrated in FIG. 6, the first control unit 19 has the function of performing a velocity control function and comprises two control elements 17 and 18. The second control unit 20 on the other hand has the function of performing a position control function and comprises the control elements 16, 17, and 18, wherein the control elements 17 and 18 of both control units 19, 20 can be used in conjunction. The control units 19, 20 or rather the control elements 16-18 can optionally be configured as hardware and/or software.

In the first control unit 19, the control signals (S1) generated by the non-dominant hand 13 are first fed into a control element 17, which generates a corresponding velocity command v. The velocity command v is then fed into another control element 18, which generates one or more control variables l1 to l3 on the basis of the velocity command for controlling one or more actuators of the robot system (e.g., one or more joints 4, the robot head 51 and/or the end effector 46). The control variables l1 to l3 can be, for example, currents for powering electric motors, in particular those of the joints 4.

In the second control unit 20, the control signal (S2) of the dominant hand 12 is first fed into a control element 16, which generates a position command x. The position command x is then converted by the control element 17 into a velocity command v and lastly fed into the control element 18, which in turn generates all of the control variables l1 to l3 that are needed for moving the robot system in accordance with the control instruction of the user. The position command x thus causes the controlled object first to accelerate and then to slow in a very precise manner so that it (e.g., one or more joints 4, the robot head 51, and/or the end effector 46) accurately performs the movement corresponding to the control instruction. To this end, a position, velocity, and/or acceleration profile can be implemented in the control unit 20, for example, wherein said profile can contain different signal amplification factors.

The first control device 19 is used here for coarse positioning, by means of which a robot arm or an end effector 5, for example, can be moved into a desired position. Because the control unit 19 generates velocity commands, precise positioning of the controlled object is not possible. With the velocity control function, however, an object can be driven faster and the dynamics of the robot 1 is thus improved. In contrast, a fine positioning of the controlled object is possible with the position control function performed by the second control unit 20.

If the user controls the same actuator or actuators simultaneously with both hands, the respective control signals S1 or S2 coming from the input 15 and the position command x coming from the control element 16 are superimposed in the control element 17 and a superimposed signal v is generated, which is in turn fed into the control element 18. In this manner a synchronous coarse and fine positioning of an object to be controlled is achievable.

In principle each movable or actuatable element of the robot 1 can be controlled individually by the user by means of the control 6. When the robot head 51 or the tool 5 is controlled directly by the user with the robot control 6, in an advantageous embodiment of the invention the robot control 6 can then automatically and simultaneously generate the necessary commands for the joints 4 of the robot 1 so that the robot head 51 or the tool 5 will move into the desired position without the user having to control each joint 4 individually.

Figure 7:
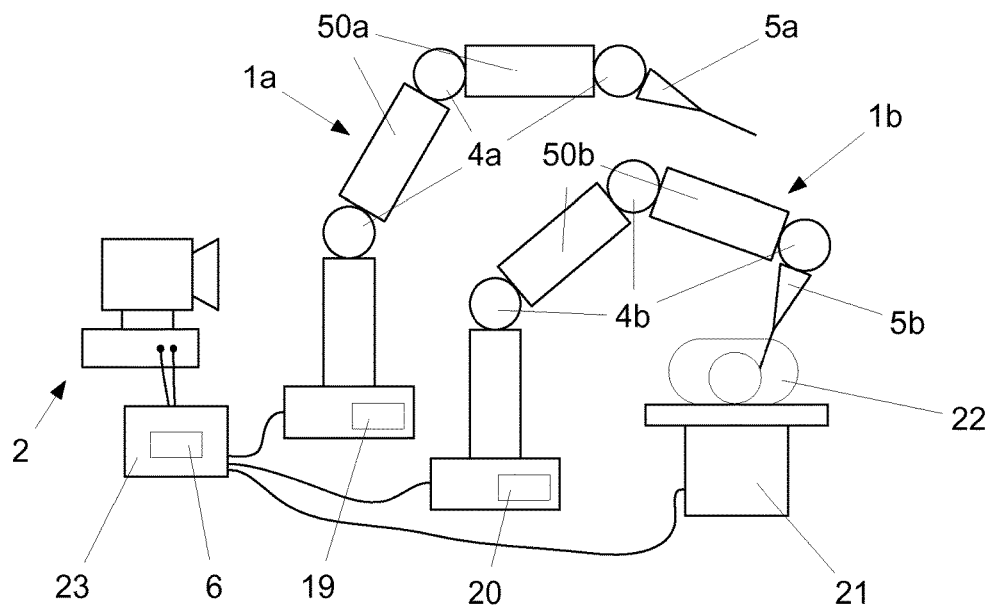
FIG. 7 a robot system with two robots for surgical use.

FIG. 7 shows a robot system with two robots 1a, 1b, which each have several arms 50a, 50b and several joints 4a, 4b. Obviously other designs are likewise conceivable. Here the robot system is configured as a surgical robot system, in particular for performing minimally invasive surgical procedures. The robots 1a, 1b are therefore equipped with special surgical instruments (such as endoscopes, trocars, tweezers, forceps, suturing devices, scalpels, spreaders, scissors, or other tools 5a, 5b as well, depending on the intended use) with which a patient 22 can be treated or moved.

The robot system further comprises an operating table 21, adjustable by electric motors, where one or more actuators can position the movable elements (e.g., back, foot, or arm rests) of the operating table 21. By appropriately adjusting the operating table, it is possible to alter the position of the patient or individual body parts of the patient and thus facilitate the operation.

The operating table 21 is connected to a control unit 23 and can be controlled therewith according to the user's control instructions. For example, the user can use the input device 2 to adjust the operating table 21 and more specifically tilt, incline, turn, adjust the height of, etc., movable elements of the operating table 21 or the entire operating table 21.

The robot control 6 for this robot system can be integrated, for example, in a control unit 23. Optionally, individual control units 19, 20 can be arranged in a distributed manner, for example in the base of the robots 1a, 1b. As an alternative, however, the robot system could also be composed of at least two full-fledged robots 1a and 1b, which each contain a complete robot control 6, as shown in FIG. 6 or FIG. 8.

The control of the robots 1a and 1b can now be effected in a manner similar to the previous embodiments, to which end both robots are connected to the control 6 (as in FIG. 6). In other words, the control element 18 can generate control signals for robot 1a as well as for robot 1b. In order to control one or the other robot alternately with the input device 2, said input device 2 can provide a selector means for coupling the control 6 to either robot 1a or robot 1b. For example, a certain hand gesture can be linked to the command for activating robots 1a and 1b alternately. Depending upon which robot is active, one or the other robot can be controlled with the input device 2.

As an alternative, each individual robot 1a, 1b can be connected to its own input device 2 and robot control 6. In this case the robot system could be operated simultaneously by several users, wherein each robot can be controlled by a different user, for example.

Figure 8:
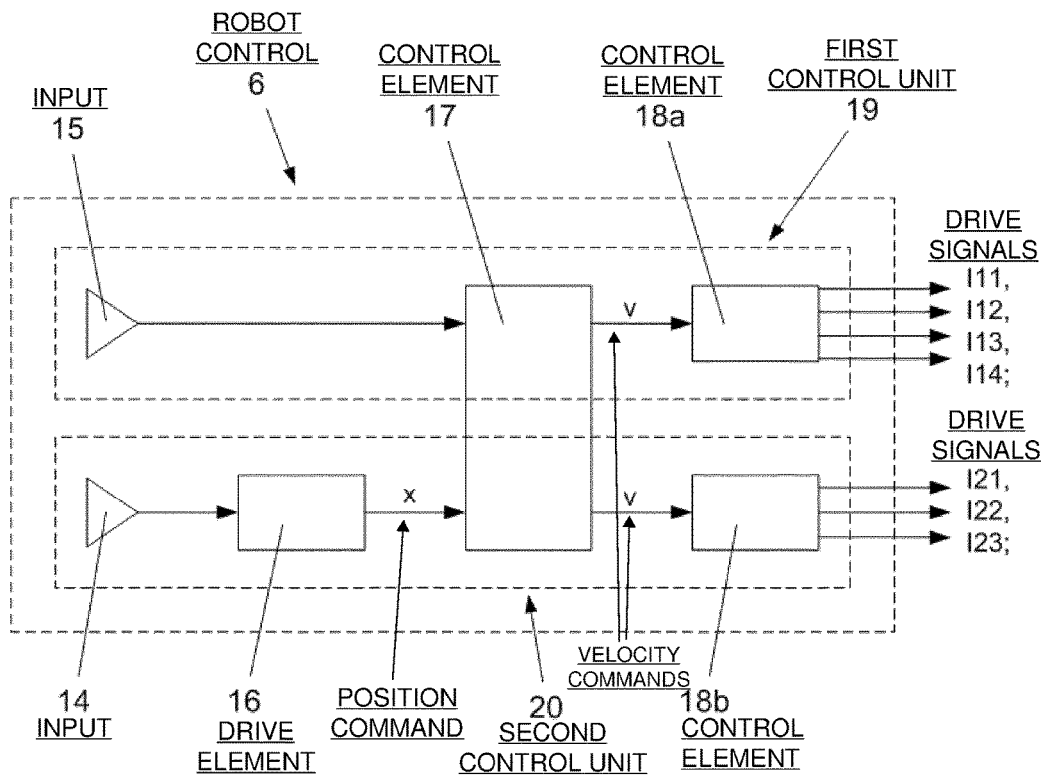
FIG. 8 a robot control for a robot system according to FIG. 7.

FIG. 8 shows an alternative robot control 6, which is designed in particular for a robot system with several robots 1a, 1b, as illustrated in example form in FIG. 7. The robot control 6 also comprises a first control unit 19 and a second control unit 20, which separately process the control signals S1, S2 received on the associated inputs 15 and 14, respectively, and convert them into corresponding output signals l11 to l13 or l21 to l23, respectively, with which the first robot 1a or the second robot 1b, respectively, are controlled. Furthermore, the first control unit 19, for example, also generates an output signal with which other mechanisms (e.g., the operating table 21) can be controlled.

In the illustrated exemplary embodiment of FIG. 8, the control unit 19 performs a velocity control function and the control unit 20 performs a position control function. Optionally, however, both control units 19, 20 could also perform a position control function. Preference is given to the control unit 19 processing the control signals generated by the non-dominant hand 13 and to the control unit 20 processing the control signals generated by the dominant hand 12.

The control signals S1 of the non-dominant hand 13 are fed via the input 15 into a control element 17, which in turn generates a corresponding velocity command v, e.g., for the robot 1a or for one or more of its actuators 4a, which is then converted by means of the control element 18a into corresponding drive signals l11-l14. The control signals S2 of the dominant hand 12 are processed by the second control unit 20, where they are fed via the input 14 into a drive element 16, which then generates a corresponding position command x therefrom. The latter is converted by the control element 17 into a velocity command v, which is in turn transformed by means of the control element 18b into corresponding drive signals l21-l23 for controlling the robot 1b or rather one or more of its actuators 4b. Hence the robot 1a is velocity controlled and the robot 1b is position controlled. Here, the operating table 21 is likewise velocity controlled, but it could also be position controlled.

A single control element 17 is used here for both control units 19, 20. As an alternative, a separate control element 17 can also be provided in each case.

The robot system can furthermore provide a selector means for changing the allocation of the controlled action to the respective hand and/or control instruction. For example, the robot 1a can thus be controlled with the dominant or the non-dominant hand, and the robot 1b with the respective other hand, as desired. The robot system can furthermore comprise an appliance with which the type of control, in particular position control or velocity control, can be selected for each hand. To this end, the user can be prompted, for example, to perform a specific gesture with the hand or to make a specific input on the system. The selection can also be made via an input mask on a computer, for example.

As has already been explained in connection with the previous embodiment of the invention, it is also possible in this embodiment to control each joint 4a, 4b individually or the two tools 5a, 5b directly. If the tools 5a, 5b are directly controlled, the robot control 6 automatically generates the necessary drive signals for controlling the joints 4a, 4b, by determining a suitable trajectory of the robot arms 1a and 1b for moving the tools 5a and/or 5b and independently maneuvering the robot arms 1a and 1b accordingly.

In a further development of the invention, it is not only possible to control the robots 1a, 1b or rather their joints 4a, 4b along with the robot head 51, but also the tools 5a, 5b themselves. As an example, FIG. 9A shows a typical surgical instrument (in this case Potts scissors) that can be used with a surgical robot system, whereas FIG. 9B shows a scalpel known from the prior art.

The various tools 5 each have several articulations with joint axes A1 to A3, about which the respective end effector 46 can be turned or pivoted. In the case illustrated here, both tools 5 each have three articulations, of which the axes A1 to A3 are each at right angles to one another. The end effectors 46 can thus carry out various spatial pivoting movements as well as rotary movements about the longitudinal axis A3.

Figure 9A:
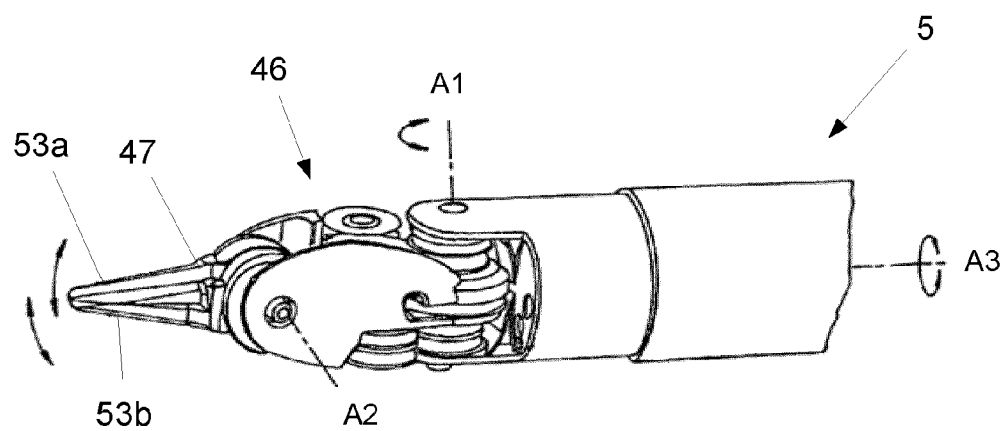
FIG. 9A Potts scissors as an example of a robot-controlled surgical instrument.
Figure 9B:
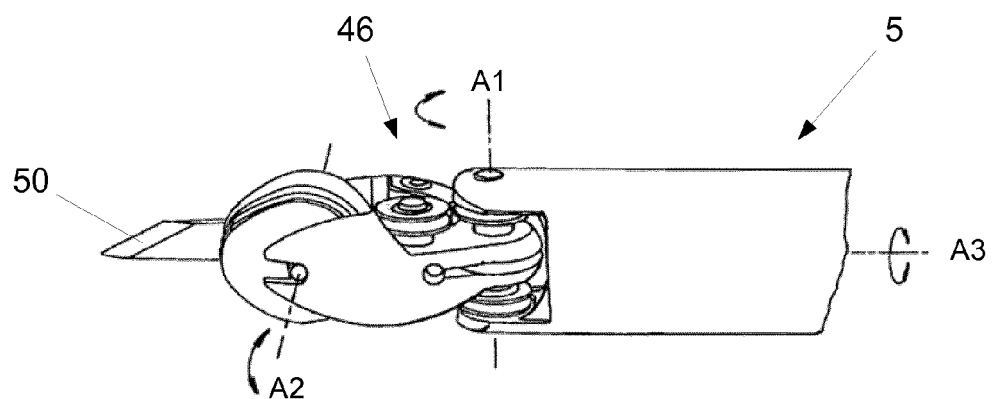
FIG. 9B a scalpel as an example of a robot-controlled surgical instrument.

The Potts scissors in FIG. 9A comprise two scissor blades 53a, 53b, which can be opened and closed along the arrows. The scalpel 50 illustrated in FIG. 9*b* can likewise be spatially pivoted and rotated about its longitudinal axis A3. The two tools 5 shown in FIGS. 9A and 9B are representative of any other tools with which the robots 1, 1a, 1b can be equipped for a given intended use.

The articulations of the tools 5 can be moved individually by means of, say, at least one electric motor-actuated drive (e.g., cable drive) integrated in the tool 5. The robot control 6 of the invention (according to FIG. 6 and/or FIG. 8) can be used for controlling each of these electric motor-powered tool drives, in a manner similar to the controlling of the robot joints 4, 4a, 4b.

For example, in order to perform a very precisely guided incision with the scalpel 50, the articulation A2 of the scalpel 50 can be subject to the position control function 20. On the other hand, merely orienting the scalpel 50 roughly via the articulation A1 may suffice and the articulation A1 could therefore be subject to a velocity control function 19. Furthermore, the finger movement 47 of the hand 12 (see FIG. 2), for example, can be recorded via the input device 2. When the input of the hand 12 is subject to the position control function, then the scissor blades 53a, 53b of the Potts scissors 47 would be precisely position-controlled. In other words, the opening angle of both scissor blades 48a, 48b would follow the respective finger placement of the hand 12 exactly. An incision can thus be made where the incision length is precisely defined by the user.

Figure 10:
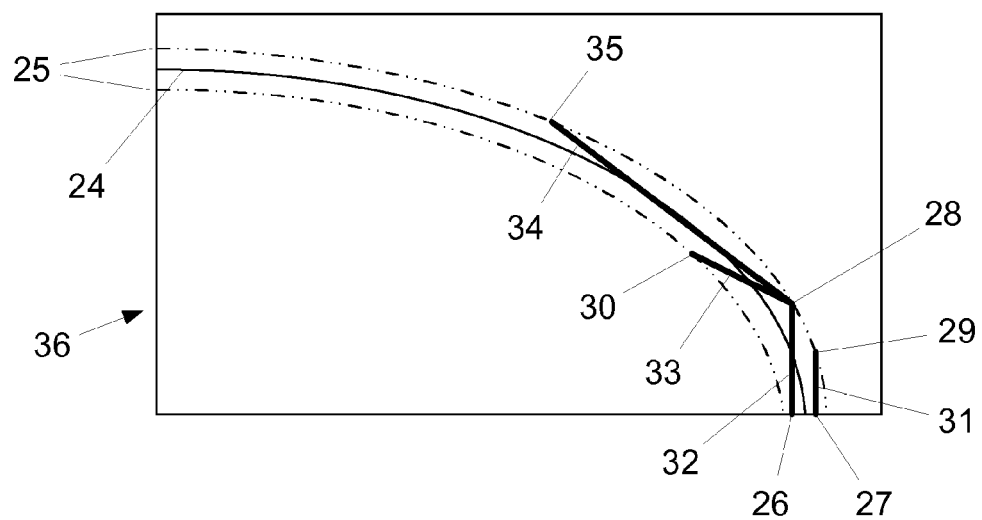
FIG. 10 a schematic illustration of human tissue to be cut using a robot-controlled surgical instrument.

FIG. 10 shows a piece of human tissue 36 to be cut using the surgical robot system of FIG. 7, for example. The incision is to be made within specified border lines 25. To make such an incision, robot 1, equipped with a scalpel, can be brought to the starting point (bottom right in the figure) by, for example, the non-dominant hand by means of velocity control.

For actuating the cutting tool 5 (e.g., scissors), the position control function 20 is now used to generate precise control instructions. The position of both blades 53a, 53b of the scissors can thus be specified precisely. An excessively wide or insufficiently wide opening or closing movement, respectively, of the scissors is thus preventable. As already mentioned above, the velocity control function 19 can be used for controlling the robot arm 1 and/or its joints 4.

Because the user can only control the instrument in a relatively imprecise manner with the coarse control function, the position in which the instrument comes to rest will likewise be imprecise and fall between, for example, points 26 and 27. When necessary, the user can use his dominant hand to correct the starting point and then perform a straight incision 31 or 32 by means of position control until he reaches the permissible boundaries 25 (see points 28 or 29). Depending upon the starting point 26 or 27, the incision within the boundaries 25 can be of different lengths. According to the invention the performance of the cutting motion is therefore position controlled, in order to control the incision length precisely. In other words, articulation A2 of the tool 5 is subject to position control. After the first incision is complete, the incision can be continued, starting from position 28 or 29. The instrument 5 must be realigned at these positions.

Consequently, a comparatively coarse positioning or alignment of the tool 5 by means of the velocity control function 19 can be compensated with the position control function 20, so that a precise incision length is achievable by the precise specification of the cutting motion. This continues in the further course of the incision process. Starting from position 28, for example, the tool 5 is repositioned or realigned by means of coarse positioning. Depending upon the angular position of the tool 5 relative to the tissue 36 or rather to the specified incision 24, the position control function 20 can prevent the cut from exceeding the tolerance boundary 25 at positions 30 or 35 by suitably adjusting the incision lengths 33, 34.

Furthermore, provision can also be made such that the user supports the incision process with his non-dominant hand 13, either by controlling the operating table 21 or by moving the body or body part being operated on (e.g., the knee of the patient 22) using a robot. The tissue piece 36 or rather the associated body part of the patient 22 can thus be guided towards the instrument 5. In the event of a curved specified incision 24 such as the one illustrated, the tissue piece 36, or rather the associated body part of the patient 22, can be moved in rotation/linearly so that even curved incisions can be performed along the specified incision 24. In other words, the position-controlled incision movement of the instrument 5 and the velocity-controlled adjustment of the object 36 are superimposed. The user can then keep his dominant hand 12 stationary and in the case of scissors, for example, simply perform opening/closing cutting motions, where the object 36 will be aligned to the scissors in accordance with the specified incision 24.

Figure 11:
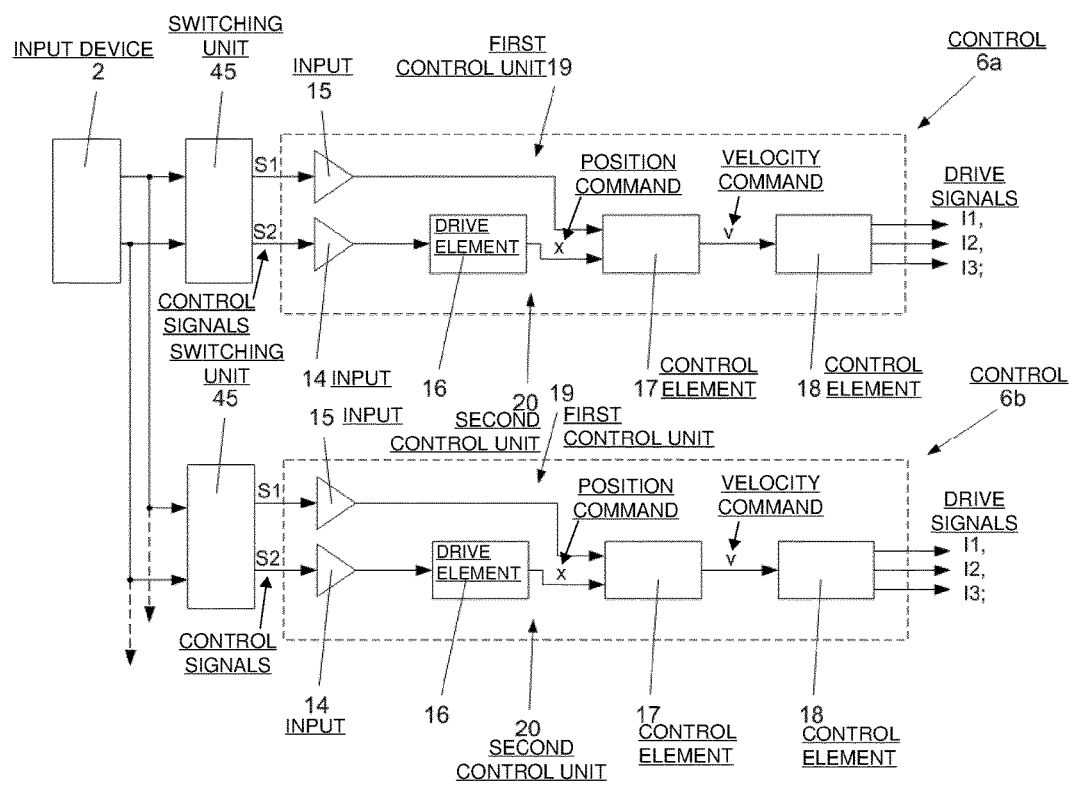
FIG. 11 a robot control according to another embodiment.

As FIG. 11 shows, it is furthermore possible to couple the input device 2 with several controls 6a, 6b, wherein each control controls different actuators of the robots 1, 1a, 1b and/or of the tools 5, 5a, 5b. In this manner, several actuators can be controlled simultaneously with the same hand motion, wherein the control form can be different. For example, a certain hand motion 49 (as illustrated in FIG. 2, for example) can cause the control 6a to actuate only the robot head 51 of a robot 1, whereas the hand motion from A to B causes the control 6b to actuate one of the other joints 4 of the robot 1.

Similarly, any number of combinations between any number of controls 6 and the actuators of the robots 1, 1a, 1b and the tools 5, 5a, 5b can be configured such that in principle all actuators of the robot system, including the tools, could be controlled simultaneously. In this respect, for example, the control 6a could be provided for actuating the robot 1a and control 6b could be provided for actuating the robot 1b.

According to the invention, it is furthermore possible for the input device 2 to distinguish hand and arm motions from one another. As shown in FIG. 5, a motion 54 of the arm 55 can be recognized as waving, independently of another hand motion or hand gesture. Accordingly, different body parts of the user can be allocated to the individual joint drives 4, 4a, 4b, 51 for controlling the robot system.

In other words, the robot arm 1a acts as a stand-in for the user's left arm, the robot arm 1b for the user's right arm, the left end effector 5a for the user's left hand, and the right end effector 5b for the user's right hand. The respective commands are generated from the hand or arm gestures recorded by the input device 2. In this manner the user is given the ability to use the robot system almost like his own two arms or hands.

The user can simultaneously effect a coarse positioning of the robot 1a or rather of the tool 5a with his non-dominant hand and a fine positioning of the robot 1b or rather of the tool 5b with his dominant hand. Since the functioning of the robot control 6 faithfully simulates the natural characteristics of a human (or rather recreates the latter's anatomy piece by piece) and adapts to the handedness of the user, it implicitly makes working with the robot system exceptionally intuitive, which characterizes the particular advantage of this alternative embodiment of the invention.

The invention claimed is:

1. A device for controlling a robot system, comprising:
   a manually operable input device including a sensor system for detecting control instructions from a first hand and from a second hand;
   a control including:
      a first control unit configured to perform a position control function based on the control instructions of the first hand, and
      a second control unit configured to perform a velocity control function based on the control instructions of the second hand; and
   an appliance configured to:
      recognize a dominant hand and a non-dominant hand of a user, and
      generate information on handedness of the user,
   wherein the control is further configured to take into account the information on the handedness of the user generated by the appliance while automatically performing the position control function in response to control instructions from the dominant hand and automatically performing the velocity control function in response to control instructions from the non-dominant hand.

2. The device as in claim 1, wherein the first and second control units are further configured to translate a control instruction carried out by the user, in each case using a specific scaling factor, into a corresponding movement of a controlled object, wherein a scaling factor of the second control unit, which is allocated to the non-dominant hand, is greater than a scaling factor of the first control unit, which is allocated to the dominant hand.

3. The device as in claim 1, wherein the control includes a control element configured to:
   superimpose a first signal, which represents a control instruction from a first hand on a second signal, which represents a position command, resulting from a control instruction from a second hand, and
   generate an output signal by which at least one actuator of the robot system is driven in order to convert the control instructions performed by the hands into a corresponding motion.

4. The device as in claim 1, wherein the first control unit and the second control unit are further configured to control the same actuator or actuators of one or more robots or of one or more tools.

5. The device as in claim 1, wherein the first control unit and the second control unit are configured to control different actuators of one or more robots or of one or more tools.

6. The device as in claim 1, wherein the sensor system comprises an imaging system with at least one camera.

7. A method for controlling a robot system by at least two hands, wherein control instructions from a first hand and from a second hand are detected by an input device, the method comprising:
   detecting an input of the first hand or the second hand;
      determining whether the first hand is a dominant or non-dominant hand or whether the second hand is the dominant or non-dominant hand, wherein information on handedness of a user is taken into account by a control including a first and a second control unit;
      processing control instructions from the dominant hand by the first control unit, which performs a position control function in response to the control instructions of the dominant hand; and
      processing control instructions from the non-dominant hand by the second control unit, which performs a velocity control function in response to the control instructions of the non-dominant hand.

8. The method as in claim 7, wherein the position control function performs a fine positioning of at least one actuator of a robot or of a tool, and the velocity control function performs an adjustment of an object or a coarse positioning of at least one actuator of a robot or of a tool.

9. The method as in claim 8, wherein inaccuracies in the velocity control function are compensated by the position control function.

* * * * *